United States Patent [19]
Rochte

[11] Patent Number: 5,233,884
[45] Date of Patent: Aug. 10, 1993

[54] FLEXIBLE CONNECTOR FOR LINEAR MOTION SYSTEMS

[76] Inventor: Jerry E. Rochte, 196 Sunkist La., Los Altos, Calif. 94022

[21] Appl. No.: 847,370

[22] Filed: Mar. 6, 1992

[51] Int. Cl.⁵ ............................ G05G 1/00; F01B 9/00
[52] U.S. Cl. ...................................... 74/581; 74/89.17; 74/110; 92/137
[58] Field of Search ...................... 74/89.17, 110, 581; 92/137; 128/DIG. 1

[56] References Cited

U.S. PATENT DOCUMENTS

| | | | |
|---|---|---|---|
| 1,775,289 | 9/1930 | Marks | 74/581 |
| 2,666,658 | 1/1954 | Laucks | 92/137 |
| 3,156,236 | 11/1964 | Williamson | 128/DIG. 1 X |
| 3,515,034 | 6/1970 | Eklund | 74/581 |
| 3,667,552 | 6/1972 | Gordon | 92/137 X |
| 4,539,854 | 9/1985 | Bradshaw et al. | 73/864.18 |
| 4,702,117 | 10/1987 | Tsutsumi et al. | 74/89.17 |

FOREIGN PATENT DOCUMENTS 2801528 4/1979 Fed. Rep. of Germany ... 128/DIG. 1

OTHER PUBLICATIONS

Using Shape Memory Alloys by Darel E. Hodgson (1988) Shape Memory Applications Inc.

*Primary Examiner*—Rodney H. Bonck
*Assistant Examiner*—Ryan W. Massey
*Attorney, Agent, or Firm*—Julian Caplan

[57] ABSTRACT

A connection between a drive member and a driven member comprises a first nickel titanium alloy wire interconnecting the drive member and a rigid link and a second nickel titanium alloy wire connecting the rigid link and the drive member. Such a wire, when properly heat treated, has a high tensile and also a high compressive strength while at the same time the wire will bend readily if there is misalignment between the longitudinal movements of the drive and driven members. Thus the assembly functions as a two-ball joint drive line similar to that used in automobiles. A preferred usage is in driving the plunger of a syringe in a dosage metering system from a moving machine element where the syringe bore and direction of movement of the machine element may be slightly out of alignment. Wear of the syringe seals is reduced.

4 Claims, 1 Drawing Sheet

FLEXIBLE CONNECTOR FOR LINEAR MOTION SYSTEMS

BACKGROUND OF THE INVENTION

1. Field of the Invention

This invention relates to a new and improved flexible connector between a drive member and a driven member in a linear motion system. More particularly, the invention relates to a connection between a drive member and a driven member comprising at least one length of nickel-titanium alloy wire interconnecting the drive member and a rigid link and may further comprise a second length of nickel-titanium alloy wire interconnecting the link and the driven member.

2. Prior Art

This invention relates to a problem which arises in linear motion systems when several parts of a machine are connected together and each part must be maintained exactly in line with the others. Heretofore, it has been necessary to provide for very precise alignment or, alternatively, for some method of accommodating or adjusting the parts in order for them to remain in line. These solutions to the problem add to the cost and complexity of the assembly.

In the prior art, manufacturers have attempted ways to allow parts to be flexibly connected such that the side loads are minimized while forcibly restraining the parts with respect to each other. Such efforts have not been totally successful because by the time sufficient flexibility has been built into the materials used for the anchor points to provide the necessary compliance, they also permitted the parts to flex in a longitudinal direction, thereby reducing the ability to precisely position the parts. In other words, the system becomes "spongy".

Another alternative was to provide a kind of universal joint connection such as that found in drive shafts. A two-ball joint permits some misalignment without inducing significant side loading. While theoretically workable, this approach has a practical constraint in that a precise, rigid yet flexible, ball connection requires precision machining. Consequently the cost of production can be out of proportion to the general cost structure of the entire assembly.

SUMMARY OF THE INVENTION

A preferred usage of the present invention is in accurately driving the plunger of a syringe in a dosage metering system where precise linear movement of the driven member from the drive member is essential so that the dosage is precise. A linear drive mechanism is connected to the plunger of a syringe. It is important not to side load the syringe and plunger assembly because if that were the case the wear of seals in the syringe would be increased.

In a typical installation, the needle end of the syringe is mounted rigidly and the outer end of the plunger is attached to the moving machine element which drives the syringe. The attaching mechanism at these two points is rarely precise enough to maintain the syringe barrel and the plunger axis in absolute alignment. Typically, there is some significant misalignment between the two axes and, in addition, often a lateral displacement between the two axes, causing the seal at the end of the plunger to be cocked inside the syringe and sideloaded so that it (or its seal) wears at an excessive rate as it is pushed against the side of the syringe barrel.

In accordance with the present invention, wires of nickel-titanium alloy are used. However, other shape memory alloys may be used. Such an alloy, when formed into wire and properly heat treated, has basic tensile strength but the wire becomes rubbery in its behavior when its strain is kept below three to five percent. The result of this behavior is that for a short length of the material of small diameter a few pounds of force can be exerted in a longitudinal direction without any effective elasticity being evident, thereby creating an effectively rigid connection while at the same time the wire will bend quite readily and compensate for misalignment of the axes of the barrel and plunger.

In accordance with the invention, the barrel of the syringe is small and receives a short piston or plunger carrying seals. Attached at the center along the axis of the plunger is a short length of nickel-titanium wire about one inch long followed by a link of relatively rigid stainless steel tubing (perhaps two inches long) and then another one-inch length of wire attached to the driving member. When arranged in this manner, the two pieces of wire act as a universal joint pair as in misaligned drive shafts.

Alternatively the rigid member may be fixed to the driven member (plunger) and the shape memory wire use to inter connect the rigid member and the drive member.

BRIEF DESCRIPTION OF THE DRAWINGS

The accompanying drawing, which is incorporated in and form a part of this specification, illustrates an embodiment of the invention and, together with the description, serve to explain the principles of the invention.

DETAILED DESCRIPTION OF THE PREFERRED EMBODIMENTS

Figure 1:
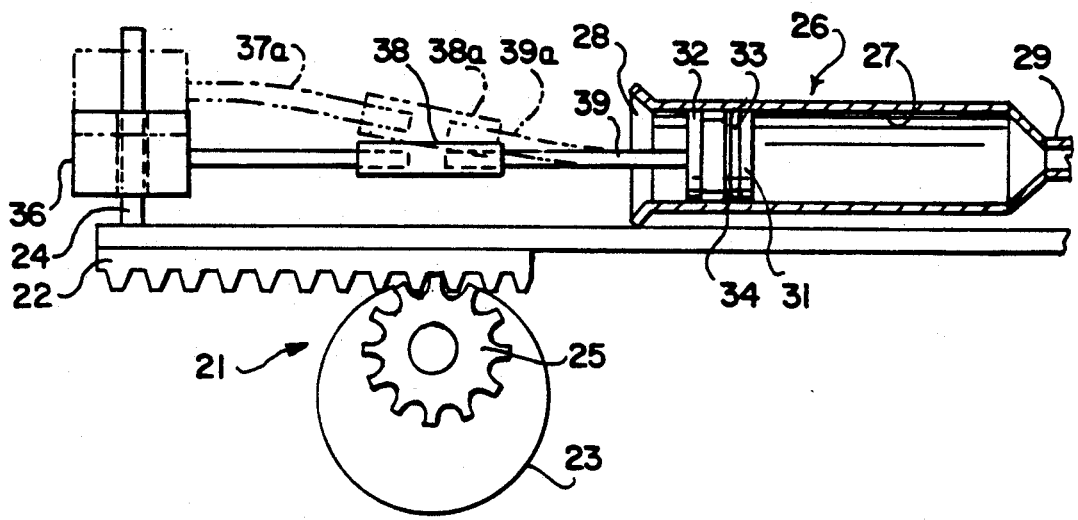
FIG. 1 is a schematic side elevational view of a portion of a dosage metering system with parts partially broken away in section to reveal internal construction showing proper alignment of the parts in solid lines and misalignment in dotted lines.

Reference will now be made in detail to the preferred embodiments of the invention, examples of which are illustrated in the accompanying drawing. While the invention will be described in conjunction with the preferred embodiment, it will be understood that it is not intended to limit the invention to that embodiment. On the contrary, the invention is intended to cover alternatives, modifications and equivalents, which may be included within the spirit and scope of the invention as defined by the appended claims.

Drive mechanism 21 may be of various types such as that shown in U.S. Pat. No. 4,539,854. A "rack" 22 is driven by a reversible motor 23 through pinion 25 and is attached to a drive pin 24. Drive pin 24 reciprocates along a first linear line from left to right, as shown in FIG. 1, in a precise, controlled manner.

Generally aligned as accurately as possible with the axis of pin 24 is the axis of a syringe 26 having a barrel 27 formed with an open end 28 and a discharge end 29. End 29 may be connected through a valve (not shown) to draw metered quantities of liquid into the barrel 27 and then, after the valve has been changed in position, to discharge a metered quantity of such fluid into an appropriate receptacle.

Reciprocable within barrel 27 along a second linear line of motion is a plunger or piston 31 having a bearing surface 32 which bears against the inside of the barrel 27 and further is formed with an O-ring-type seal 33 which fits into a groove 34 in the plunger 31. An important feature of the present invention is the reduction in wear on the bearing surface 32 and seal 33 accomplished by provision for misalignment between the travel of the plunger 31 and movement of the drive pin 24 which occurs when the first and second linear lines of motion are misaligned.

Accordingly, as shown in FIG. 1, a connector 36 is placed on the pin 24, the pin and connector preferably being formed with mating threads for accurate positioning. Fixed to connector 36 is a short (i.e., about 1 inch) shape memory alloy were such as length of nickel titanium wire 37 of approximately 0.05 in. diameter. An end of wire 37 fits inside and is fixed to a two-inch steel tube 38 which is quite rigid. The opposite end of tube 38 is connected to a second piece of wire 39 preferably identical to the wire 37 and the remote end of wire 39 is fixed to the plunger 31.

As shown in dotted lines, if there is a misalignment between connector 36 and the barrel 27, nevertheless accurate longitudinal movement of the plunger 31 will be accomplished dependent on the movement of the pin 23. The tensile and compressive strength of the wires 37 and 39 is not affected by bending thereof.

Nickel titanium alloy when formed into wire and properly heat treated takes on the general characteristics of cooked spaghetti—the basic tensile strength of the material remains quite high but it becomes rubbery in its behavior when its strain is kept below 3 to 5 percent. The result of this behavior is that for short lengths of the material of small diameter a few pounds of force can be exerted in a longitudinal direction without any effective elasticity being evident, thereby creating an effectively rigid connection while at the same time the wire will bend quite readily and compensate for misalignment.

In the foregoing description, 50-50 NiTi alloy has been specified as a preferred material of construction for wires 37 and 39. However, the following Table shows other alloys having shape memory effects.

TABLE

| Alloy | Composition |
| --- | --- |
| AgCd | 44~49 at % Cd |
| AuCd | 46.5~50 at % Cd |
| CuAlNl | 14~14.5 wt % Al |
|  | 3~4.5 wt % NL |
| CuSn | ~15 at % 5n |
| CuZn | 38.5~41.5 wt % Zn |
| CuZn X | few wt % X |
| (X = Sl, Sn, Al) |  |
| InTl | 18-23 at % Tl |
| NlAl | 36~38 at % Al |
| NlTl | 49~51 at % Nl |
| FePt | ~25 at % Pt |
| MnCu | 5~35 at % Cu |

TABLE-continued

| Alloy | Composition |
| --- | --- |
| FeMnSl | 32 wt % Mn, 6 wt % Sl |

The above table is derived from the publication "Using Shape Memory Alloys" by Darel E. Hodgson, Ph.D., 1988.

Figure 2:
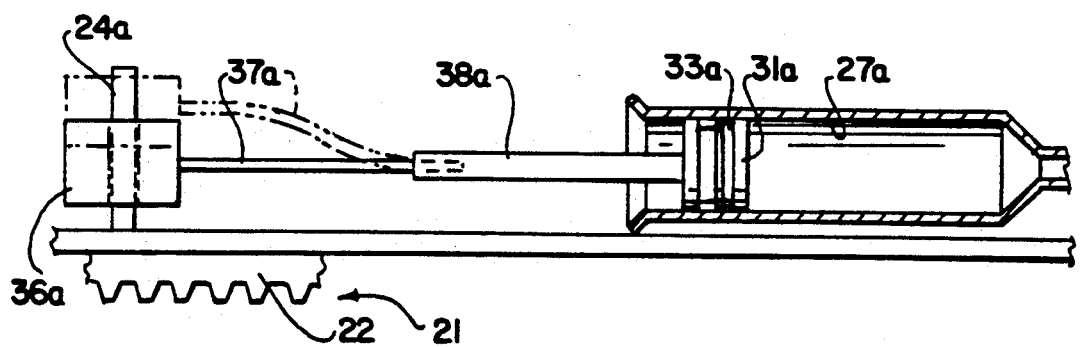
FIG. 2 is a view similar to FIG. 1 of a modification.

A modification of the invention is shown in FIG. 2. Here the rigid tube 38a is fixed to plunger 31a and a single flexible wire 37a (similar to wires 37 and 29 of the modification of FIG. 1) connects tube 38a to connector 36a of drive pin 24a. In other respects many of the elements of FIG. 2 resemble these of FIG. 1 and the same reference numerals followed by subscript a designate corresponding parts.

The foregoing descriptions of a specific embodiment of the present invention has been presented for purposes of illustration and description. It is not intended to be exhaustive or to limit the invention to the precise forms disclosed, and obviously many modifications and variations are possible in light of the above teaching. The embodiments was chosen and described in order to best explain the principles of the invention and its practical application, to thereby enable others skilled in the art to best utilize the invention and various embodiments with various modifications as are suited to the particular use contemplated. It is intended that the scope of the invention be defined by the claims appended hereto and their equivalents.

I claim:

1. In combination, a syringe cylinder, a flexible connector, a drive member having reciprocating linear movement along a first line, a piston in said syringe cylinder having a reciprocating linear movement by reason of said connector interconnecting said drive member and said piston along a second line and wherein said first and second lines are susceptible to being slightly out of alignment comprising
    a short piece of thin, flexible wire of a nickel-titanium alloy adapted to be secured to the drive member at a first end of said first wire,
    a short, rigid tubular link having embedded in its first end a second end of said first wire, said link being approximately twice the length of said wire,
    means interconnecting a second end of said link and said piston, said means fitting within said link,
    said wire being of a type without substantial elasticity when force is exerted in a longitudinal direction while at the same time bending readily to compensate for misalignment of said first and second lines.

2. A connector according to claim 1 in which said alloy is approximately 50% nickel and approximately 50% titanium.

3. A connector according to claim 1 in which said means comprises a second short piece of wire similar to said first-mentioned piece having a first end attached to said second end of said link and its second end adapted to be secured to said piston.

4. A connector according to claim 3 in which each said wire is of approximately one inch in length and approximately 0.05 in. in diameter.

* * * * *